United States Patent
Bolz

(10) Patent No.: US 7,144,494 B2
(45) Date of Patent: Dec. 5, 2006

(54) CIRCUIT ARRANGEMENT FOR COMPENSATING INTERFERENCE SIGNALS IN THE CONTROL LOOP OF A LINEAR LAMBDA PROBE

(75) Inventor: Stephan Bolz, Pfatter (DE)

(73) Assignee: Siemens Aktiengesellschaft, Munich (DE)

( * ) Notice: Subject to any disclaimer, the term of this patent is extended or adjusted under 35 U.S.C. 154(b) by 505 days.

(21) Appl. No.: 10/341,098

(22) Filed: Jan. 13, 2003

(65) Prior Publication Data

US 2003/0178303 A1    Sep. 25, 2003

Related U.S. Application Data

(63) Continuation of application No. PCT/DE01/02571, filed on Jul. 10, 2001.

(30) Foreign Application Priority Data

Jul. 12, 2000    (DE)    ................... 10033730

(51) Int. Cl.
*G01N 27/41* (2006.01)
(52) U.S. Cl. ................... 205/784.5; 204/406; 204/425; 123/694
(58) Field of Classification Search ............. 205/784.5; 204/406, 425, 427; 73/23.21, 23.31, 23.32; 123/694, 695
See application file for complete search history.

(56) References Cited

U.S. PATENT DOCUMENTS 3,906,381 A * 9/1975 Bennett .................. 327/344
6,289,719 B1 * 9/2001 Bloemer et al. ........... 73/23.21

FOREIGN PATENT DOCUMENTS

| DE | 197 22 872 A1 | 3/1998 |
| WO | WO99/18429 | 4/1999 |

OTHER PUBLICATIONS

Diefenderfer, Principles of Electronic Instrumentation, 2nd edition, Saunders College Publishing, pp. 37-41, 222, 223, 1979.*
Abstract for JP 09-065480, Jul. 1997.

* cited by examiner

Primary Examiner—Kaj K. Olsen
(74) Attorney, Agent, or Firm—Baker Botts, L.L.P.

(57) ABSTRACT

A compensation circuit (KS) is provided between the output of a differential amplifier (Diff_Amp) and the input of a controller (R). The compensation circuit generates a compensation signal, whose characteristic curve approximates to that of the parasitic signal, with the same amplitude and frequency (Phi1) as the parasitic signal, but by 180 DEG out of phase. The compensation signal is subtracted from the differential signal (DELTA Vs) and allows the parasitic signal to be eliminated to a great extent.

16 Claims, 14 Drawing Sheets

PRIOR ART

CIRCUIT ARRANGEMENT FOR COMPENSATING INTERFERENCE SIGNALS IN THE CONTROL LOOP OF A LINEAR LAMBDA PROBE

CROSS REFERENCE TO RELATED APPLICATION

This application is a continuation of copending International Application No. PCT/DE01/02571 filed Jul. 10, 2001, which designates the United States, and claims priority to German application number 100 33 730.9 filed Jul. 12, 2000.

BACKGROUND OF THE INVENTION

The invention relates to a circuit arrangement for compensating interference signals in the control loop of a linear lambda probe according to the features of the preamble of claim 1.

Legislators are using tax measures to promote the development of motor vehicles with lower fuel emissions and lower consumption of fuel.

In spark ignition engines with stoichiometric mixture formation ($\lambda=1$) this has led to the development of SULEV vehicles (Super Ultra Low Emission Vehicles) with extremely low emissions.

In order to save fuel, engines with direct high pressure injection of gasoline (HPDI, High Pressure Direct Injection) are currently being developed and introduced into the market. The fuel here is injected directly into the combustion space at increased pressure (approximately 150 bar). The conditioning of the mixture which is possible in this way can vary between rich, stoichiometric and lean. For the partial load operating mode of the engine a lean mixture formation offers considerable advantages in terms of consumption.

Both developments require a significantly more precise control of the mixture than is possible with currently customary lambda probes (binary step change probes). In addition, by binary step change probes have an extremely restricted measuring range around $\lambda=1$. They are therefore unsuitable for measurements in the lean operating mode $\lambda>1$.

For this reason, lambda probes with an extended linear measuring range, which are referred to as linear lambda probes, and circuit arrangements for operating them are being increasingly used.

FIG. 1 shows a linear lambda probe which is known per se. It has a heating element H, two electrode pairs VsC and IpC and a measuring chamber Mk which is connected to the exhaust gas stream A via a diffusion barrier GDP. The first electrode pair VsC is arranged between the measuring chamber Mk and air L and is used—similarly to the step jump probe—to measure the oxygen concentration in the measuring chamber Mk. The second electrode pair IpC is arranged between the measuring chamber Mk and the exhaust gas stream A. It permits—when a current Ip of appropriate polarity is applied—oxygen ions to be pumped out of the measuring chamber Mk or into it; hence the designation pump electrodes.

It is thus possible to generate a dynamic equilibrium between the flow of oxygen through the diffusion barrier and the flow of oxygen ions through the pair of pump electrodes. A suitable controlling criterion here is the oxygen concentration in the measuring chamber Mk which is determined using the measuring electrodes. A preferred value is, for example, Vs=450 mV for $\lambda=1$.

The pumping current Ip which flows in this case is a measure of the oxygen concentration in the exhaust gas. (And also of $\lambda$ after numerical conversion).

Some lambda probes require an artificial oxygen reference for operation. This is produced by pumping oxygen out of the measuring chambers to the positive reference electrode Vs+ by means of a small current Icp (for example 25 µA). The oxygen concentration which is produced as a result is then used for its part as a reference point for measuring the oxygen concentration in the measuring chamber Mk. The evaluation circuit must make this current available.

The relationship between the oxygen concentration in the exhaust gas and the pumping current Ip is influenced by a number of probe parameters. For reasons of fabrication, the dynamic resistance of the diffusion barrier fluctuates. This would result in a deviation of the transmission ratio (gain errors). During fabrication, this is compensated by measuring and inserting a calibrating resistor Rc into the probe plug.

FIG. 2 shows a basic circuit diagram of a known device for operating a linear lambda probe of an internal combustion engine.

A first terminal Vs+, a second terminal Vp−/Vs−, a third terminal Vp+ and a fourth terminal Rc extend out of the probe S and are connected to the evaluation circuit. The probe heater and its terminals are not illustrated.

The inverting input of a controller is connected to the first terminal Vs+ of the probe S and its noninverting input is connected to a center voltage Vm (Vm≈Vcc/2) via a reference voltage Vref, Vcc (usually 5 V) being a supply voltage of the circuit.

The second probe terminal Vp−/Vs− and the inverting input of a pumping current source Ip Pump, whose noninverting input is connected to the output of the controller, are also connected to the center voltage Vm.

The output of the pumping current source Ip Pump is connected to the fourth input Rc of the probe S.

As the resistor Rc is subjected to considerable environmental loading owing to its installation position in the probe plug, a further resistor Rp is connected in parallel with it to the terminals Vp+ and Rc in the controller. This reduces the influence of a tolerance fault of Rc on the measuring accuracy of the pumping current Ip.

The method of operation of the known circuit arrangement illustrated in FIG. 2 for operating a linear lambda probe (without generating Icp) is as follows:

The terminal Vp−/Vs− of the probe is, like the reference voltage Vref, connected to the center voltage Vm. This serves as a reference voltage of the circuit.

The control amplifier R compares the Nerst voltage Vs of the probe with the reference voltage Vref (for example 450 mV) and generates an output voltage which is converted by the subsequent pumping current source I Pump into a corresponding current Ip which then flows through the pumping cell to the center voltage Vm. The pumping current brings about a change in the oxygen concentration in the measuring chamber of the probe, which in turns results in a change in the Nernst voltage Vs. The difference between Vs and Vref (=$\Delta$Vs) constitutes the control error of the loop. The pumping current Ip can be measured as a voltage drop at the resistor Rp/Rc. It is used as measure of the oxygen concentration in the exhaust gas.

In the stable control state ($\lambda=1$ in the measuring chamber), the Nernst voltage Vs is, for example, precisely 450 mV ($\Delta$Vs=0).

Equilibrium prevails between the oxygen flow through the diffusion barrier and the oxygen ion flow, caused by the pumping current Ip. The maximum range of the output voltage of the pumping current I Pump ranges from approximately 0.1 V to 4.9 V.

Alternatively, the control amplifier can also be embodied as an OTA (Operational Transconductance Amplifier) whose output stages form a current source. The output signal here is already a current and not—as is customary in the case of the operational amplifier—a voltage.

Furthermore, the dynamic resistance of the diffusion barrier has a temperature dependence and pressure dependence illustrated in FIGS. 3A and 3B, respectively which in turn causes faults in the transmission ratio. The temperature dependence is counteracted by measuring the probe temperature and controlling it by means of a heating element installed in the probe. For reasons of cost, a separate thermal element is not used here. Instead, the highly temperature-dependent internal resistance of the probe (probe impedance) is measured. The pressure dependence cannot be sensed in the probe by measuring equipment. If a separate pressure sensor is not used, an attempt is made to determine the dependence by means of a model-based calculation in the microcontroller and to compensate it numerically.

FIG. 4A shows the probe impedance Ris of the probe S and its temperature dependence. The probe impedance can be represented as a temperature-dependent, complex impedance with a plurality of RC elements as shown in FIG. 4B, in which case:

R1/C1 represents the contact resistance between electrodes and ceramic material, R2/C2 represents the junction between the grain boundaries of the ceramic sintered elements, and R3 represents the intrinsic resistance of the sintered material.

As one of the electrodes of the pumping cell is subjected to the exhaust gas, its internal resistance changes to a very great extent. For this reason, the Nernst cell Vs is used to measure the probe temperature. Here too, R1 changes and should therefore not be used for measuring temperature. As the time constant R1*C1 has the highest value (lowest frequency), it is possible to reduce its influence by suitable selection of the measuring frequency. The impedance of the series connection of R2/C2 and R1 is therefore measured. The impedance Ris of a typical linear lambda probe is approximately 100Ω at a temperature of approximately 500° C. to 700° C. (and a measuring frequency of 3 kHz).

Measurement of the internal resistance Ris:

A known measuring method for determining Ris is to apply an alternating current, for example 500 μA (peak-to-peak, abbreviated below to ss) to the probe terminal Vs+. As a result of this alternating current, an alternating voltage of 500 μA*100Ω=50 mV (ss) is produced at Ris and it is superimposed on the Nernst voltage Vs, the actual probe signal, as an interference signal.

FIG. 6 shows a typical voltage profile of the alternating voltage signal which forms an interference signal for the Nernst voltage. The signal is amplified in an amplifier V, for example by a factor 10, and then rectified in a rectifier GLR. The DC voltage Vri which has been produced in this way can then be fed to a microprocessor in order to control the temperature.

For example, the alternating current is generated, as illustrated in FIG. 5, by means of a 3 kHz square-wave oscillator OSZ which is supplied with a voltage Vcc. The signal is conducted to the probe terminal Vs+ via a high-impedance resistor R1 and a decoupling capacitor C1.

A basic problem of this circuit arrangement is the above-mentioned mutual influence between Vs and this interference signal as this interference signal also appears at the input of the controller and constitutes a control error. The controller will attempt to compensate this control error within the scope of its bandwidth. To do this, it changes the pumping current Ip, which in turn has effects on the Nernst voltage Vs. As the pumping current Ip is the measured variable for λ, the primary probe signal is falsified. FIG. 7 makes this fact apparent. In the case of the 3 kHz signal (upper signal), the peak and the pulse tilt are falsified by the Vs signal, and in the case of the Vs Signal (lower signal) the 3 kHz triangular signal is undesired.

SUMMARY OF THE INVENTION

The object of the invention is to reduce the interference signal which is contained in the fault signal ΔVs and is undesired for the lambda control, in such a way that it no longer influences the pumping current control.

This object is achieved according to the invention in that a compensation circuit is inserted into the pumping current circuit (FIG. 5).

An embodiment of the present invention is a circuit arrangement for compensating interference signals in the control loop of a linear lambda probe of an internal combustion engine which is connected to an evaluation circuit which has a differential amplifier which forms the difference between the Nernst voltage which is measured in the lambda probe and subjected to an interference signal caused by the measurement of the probe impedance and a reference voltage which is related to a center voltage, and having a controller which generates a controlling voltage which is assigned to the difference and which is converted into a pumping current by a subsequent pumping current source, wherein a compensation circuit which generates a compensation signal which is approximated in its curve profile to the interference signal and has an amplitude and frequency which are identical to the interference signal but phase-shifted through 180°, which compensation signal is subtracted from the differential signal and as a result largely cancels out the interference signal, is provided between the output of the differential amplifier and the input of the controller.

Another embodiment is a circuit arrangement for compensating interference signals in the control loop of a linear lambda probe comprising:

an evaluation circuit with a differential amplifier which forms the difference between a Nernst voltage which is subjected to an interference signal and a reference voltage, a controller generating a controlling voltage from the difference wherein the controlling voltage is converted into a pumping current by a subsequent pumping current source, and a compensation circuit which generates a compensation signal which is approximated in its curve profile to the interference signal and has an amplitude and frequency which are identical to the interference signal but phase-shifted through 180°, wherein the compensation signal is subtracted from the differential signal and as a result largely cancels out the interference signal, coupled between the output of the differential amplifier and the input of the controller.

The compensation circuit may contain an amplifier which is connected as a buffer and an integrator, the differential signal and the output signal of the integrator can be fed to the input of the buffer amplifier, and the output signal of the buffer amplifier can be fed to the inverting input of the integrator and to the input of the controller. The controller can be combined with the compensation circuit which contains an amplifier which is connected as an inverter and an integrator, the controller can be connected as a summing amplifier to two inputs, the differential signal can be fed to the one input of the controller, and the output signal of the controller can be fed to the input of the integrator whose output signal is fed to the second input of the controller via the inverter. The integrator may contain an integration capacitor whose polarity is reversed in synchronism with the oscillator frequency by means of an alternating switch, wherein, in the one—positive—phase, the one terminal of the integration capacitor is connected to the output of the integrator and the other terminal is connected to the inverting input of the integrator, and in the other—negative—phase the one terminal is connected to the inverting input and the other terminal is connected to the output of the integrator. The integrator may also contain at least two integration capacitors whose polarity is reversed in synchronism with the oscillator frequency by means of alternating switches in such a way that, in identical numbers of phase sections, corresponding to the number of integration capacitors, of the one—positive—phase, the first terminals of the integration capacitors are successively connected to the output of the integrator and other terminals are connected to the inverting input of the integrator, and in identical numbers of phase sections, corresponding to the number of integration capacitors, of the other—negative—phase, the first terminals are successively connected to the inverting input and the other terminals to the output of the integrator. The interference signal and the oscillator signal can be generated by means of the same signal source.

A method for compensating interference signals in the control loop of a linear lambda probe may comprise the steps of:
forming the difference between a Nernst voltage which is subjected to an interference signal and a reference voltage,
generating a controlling voltage from the difference,
converting the controlling voltage into a pumping current,
generating a compensation signal which is approximated in its curve profile to the interference signal and has an amplitude and frequency which are identical to the interference signal but phase-shifted through 180°, wherein the compensation signal is subtracted from the differential signal and as a result largely cancels out the interference signal.

BRIEF DESCRIPTION OF THE DRAWINGS

Exemplary embodiments according to the invention are explained in more detail below with reference to a schematic drawing in which.

DETAILED DESCRIPTION OF THE PREFERRED EMBODIMENTS

Figure 9:
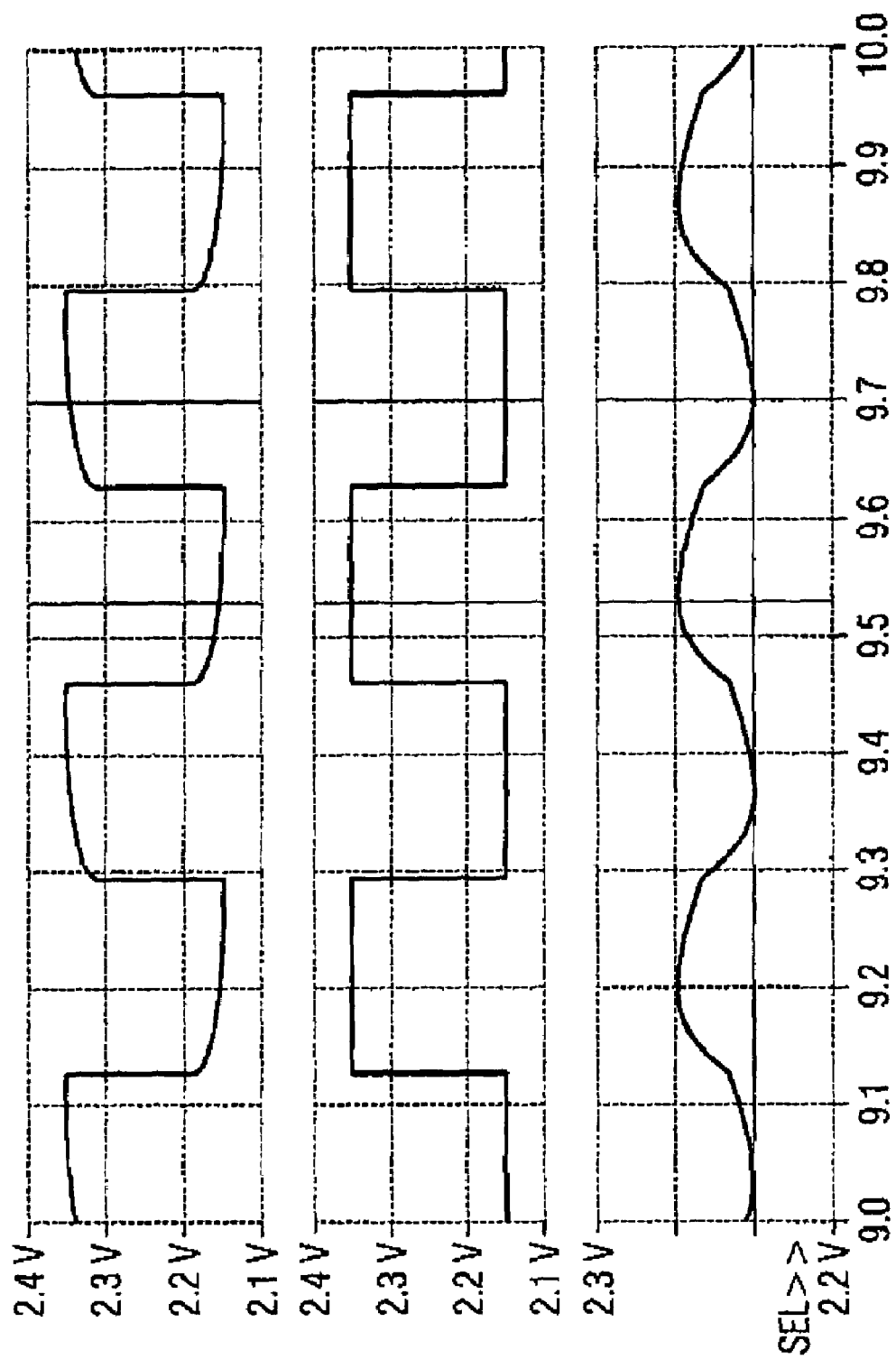
FIG. 9 shows an interference signal, compensation signal and residual signal of the circuit according to FIG. 8.

The invention is based on the idea that the amplitude of the interference signal (FIG. 6) is not known but the basic curve profile (square wave with time constant), the frequency and the phase angle are, as the generating signal originates of course from the local oscillator OSZ, V12, V15. If a further square wave (compensation signal) with the same amplitude and frequency with a 180° shifted phase is subtracted from this interference signal, as illustrated in FIG. 9, the two signals largely cancel one another out (filtering in the time domain).

The magnitude of the residual signal is determined by the following factors:
the phase difference between the interference signal and compensation signal (if both signals are generated locally, the phase difference may be negligibly small),
amplitude difference between the two signals (this is minimized with the circuit described further below),
differences in the signal profile (if the interference signal and compensation signal have different curve shapes, for example square wave with time constant and pure square wave, the time constant is retained in the residual signal but can be further reduced by incrementally approximating the curve profiles.

The interference signal and the compensation signal (FIG. 9 above and center) have amplitudes of approximately 200 mV (ss), the residual signal (FIG. 9 below) only has an amplitude of 30 mV (ss) after slight low-pass filtering ($\tau$=20 µs). The interference signal has therefore attenuated by approximately 16 dB.

Figure 1:
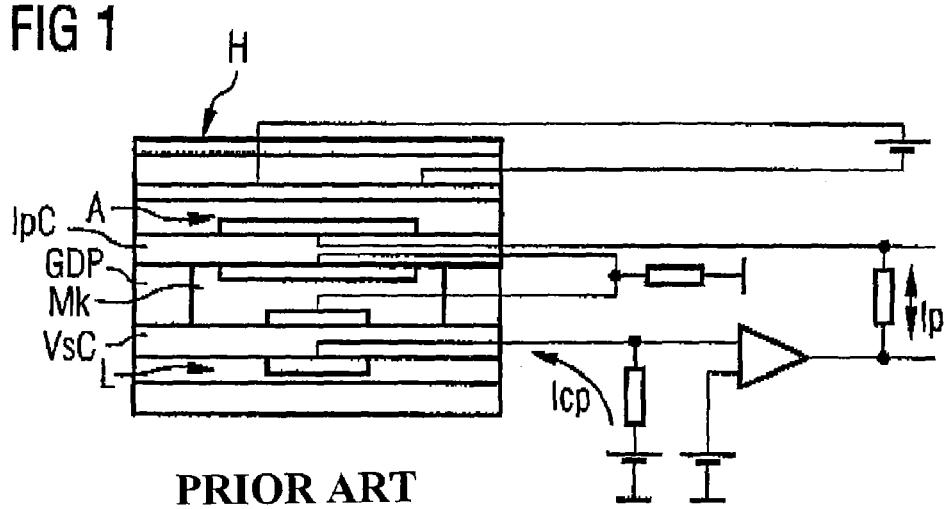
FIG. 1 shows a basic circuit of a linear lambda probe.
Figure 2:
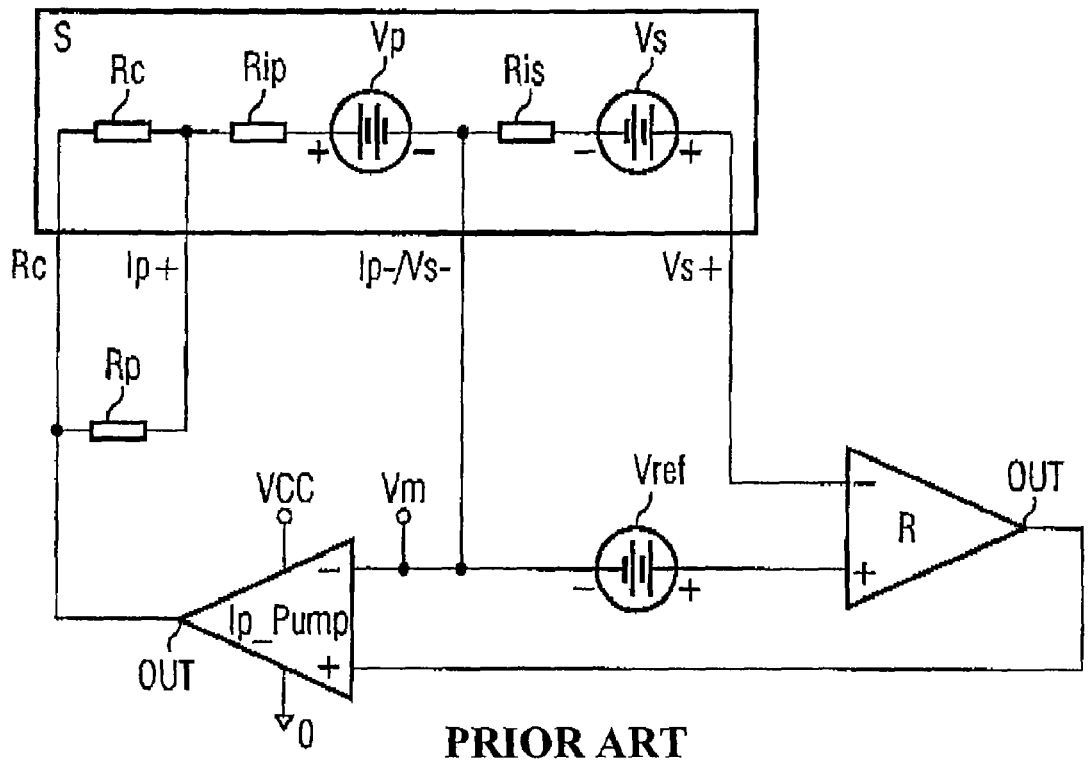
FIG. 2 shows a known circuit arrangement for operating a linear lambda probe.
Figure 3A:
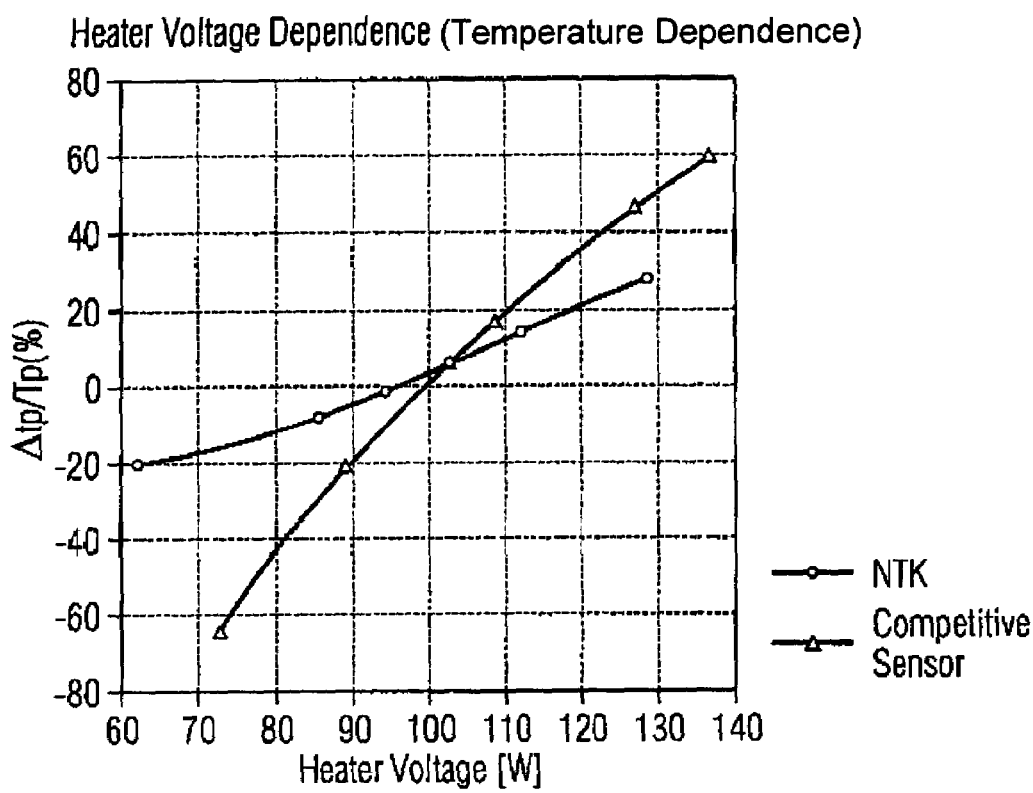
FIGS. 3A and 3B shows temperature dependence and pressure dependence of the transmission ratio of a linear lambda probe.
Figure 3B:
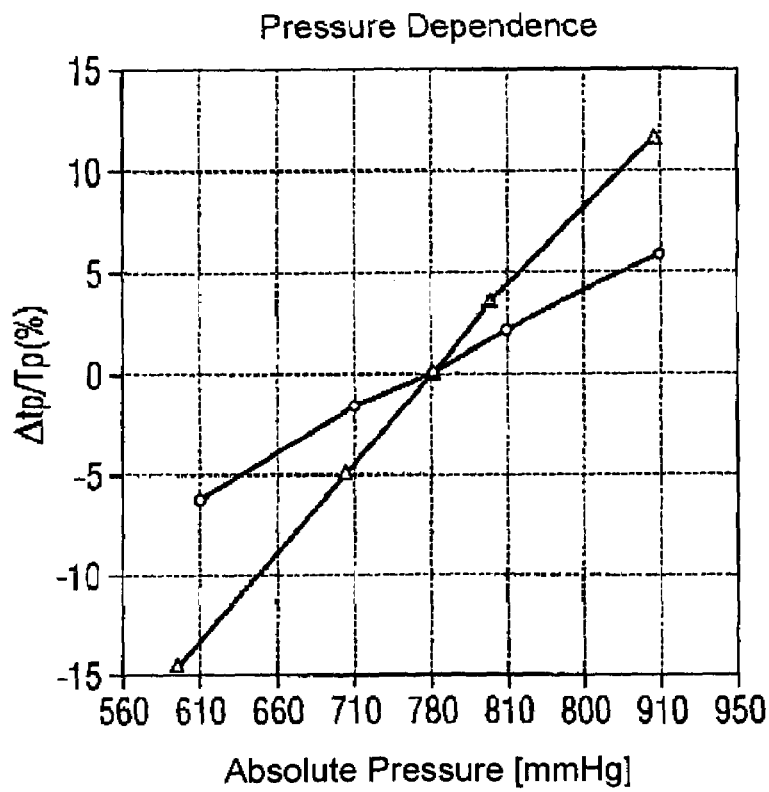
Figure 4A:
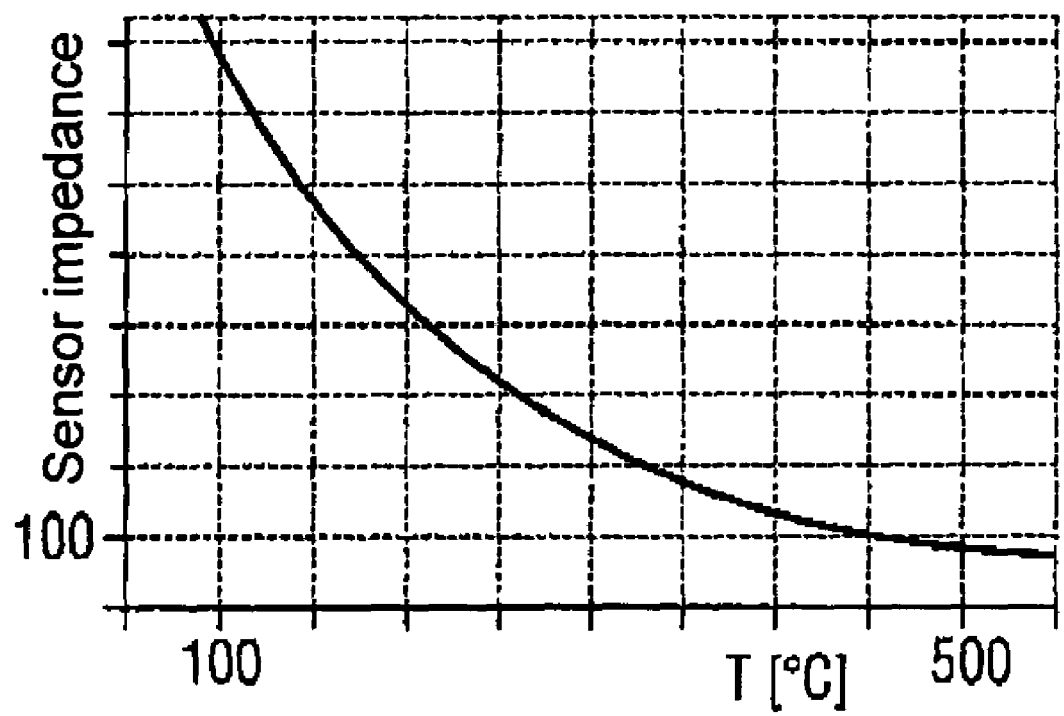
FIGS. 4A and 4B shows temperature dependence and equivalent circuit diagram of the probe impedance of a linear lambda probe.
Figure 4B:
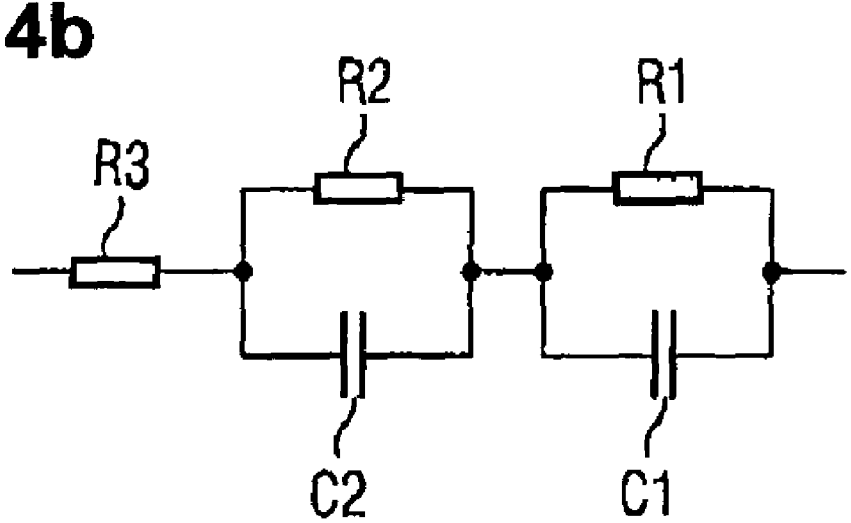
Figure 5:
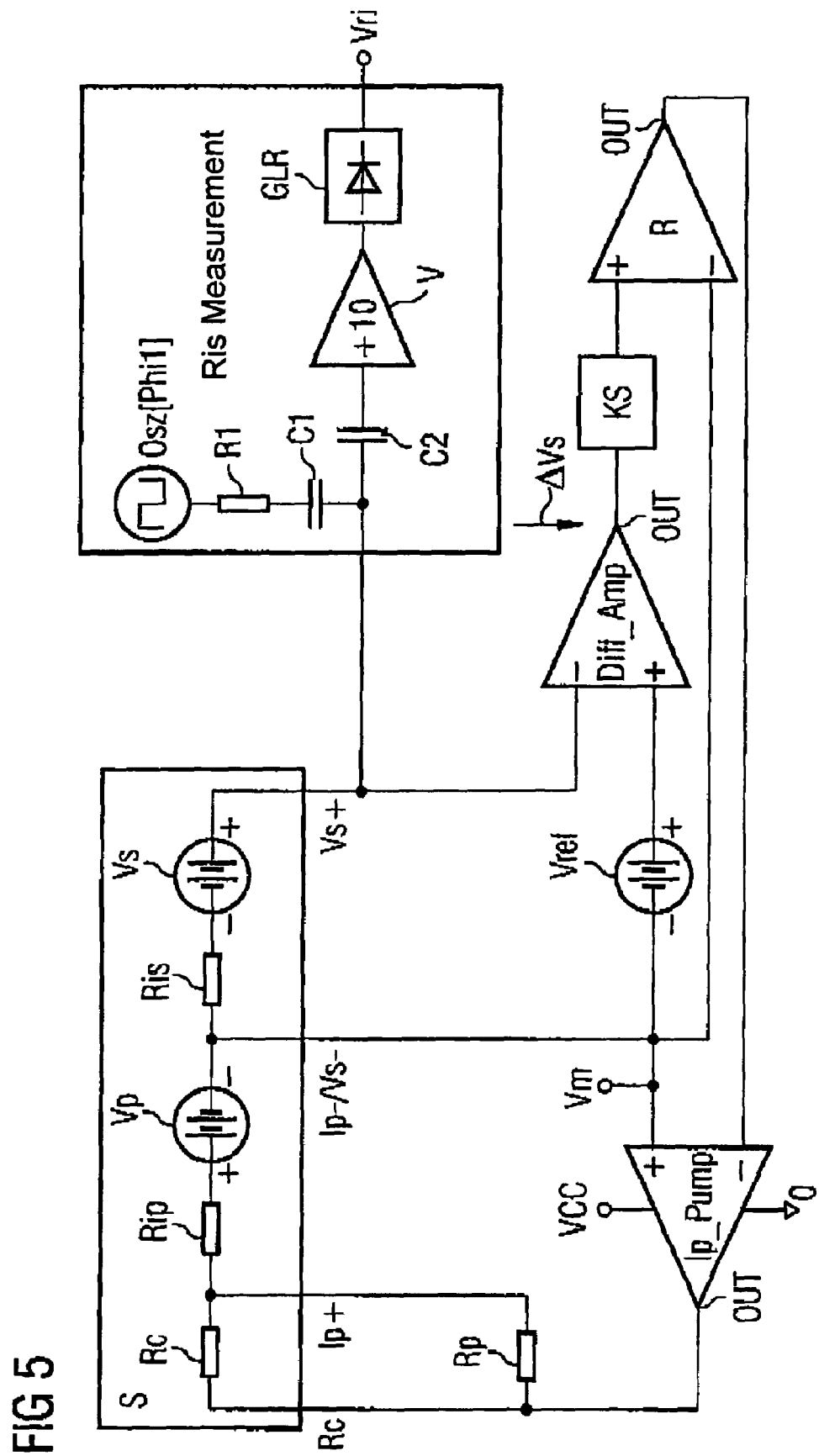
FIG. 5 shows a basic circuit arrangement for operating a linear lambda probe with a compensation circuit according to the invention.
Figure 8:
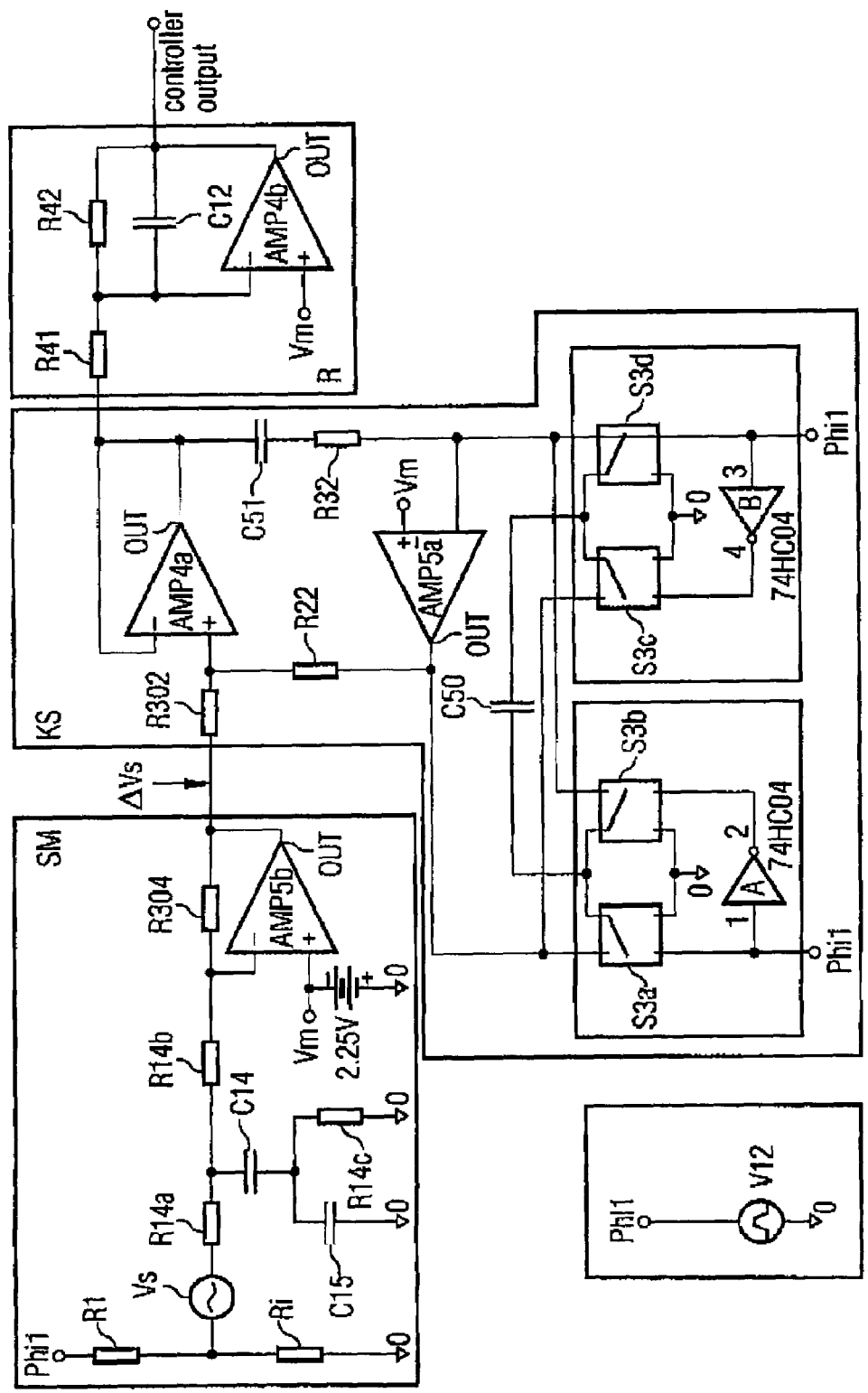
FIG. 8 shows a circuit diagram of a first exemplary embodiment of a compensation circuit.

FIG. 8 shows a circuit KS according to the invention for compensating interference signals in the control loop of a linear lambda probe. In order to represent the behavior of the compensation circuit correctly, it is considered in conjunction with a probe model SM, the controller known from FIG. 5 and the 3 kHz oscillator V12 and described in more detail with respect to its function.

Figure 6:
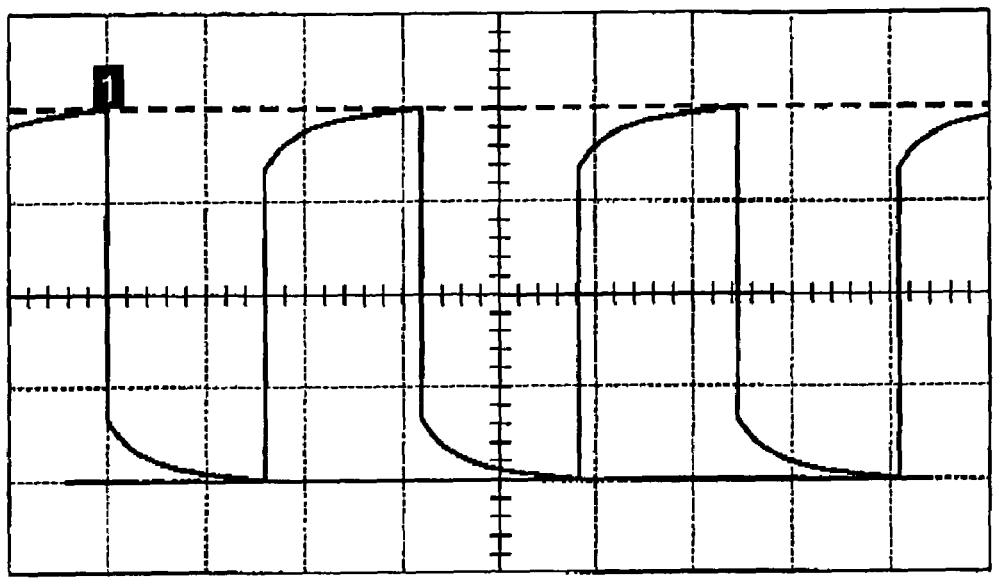
FIG. 6 shows a typical curve profile of the interference signal.
Figure 7:
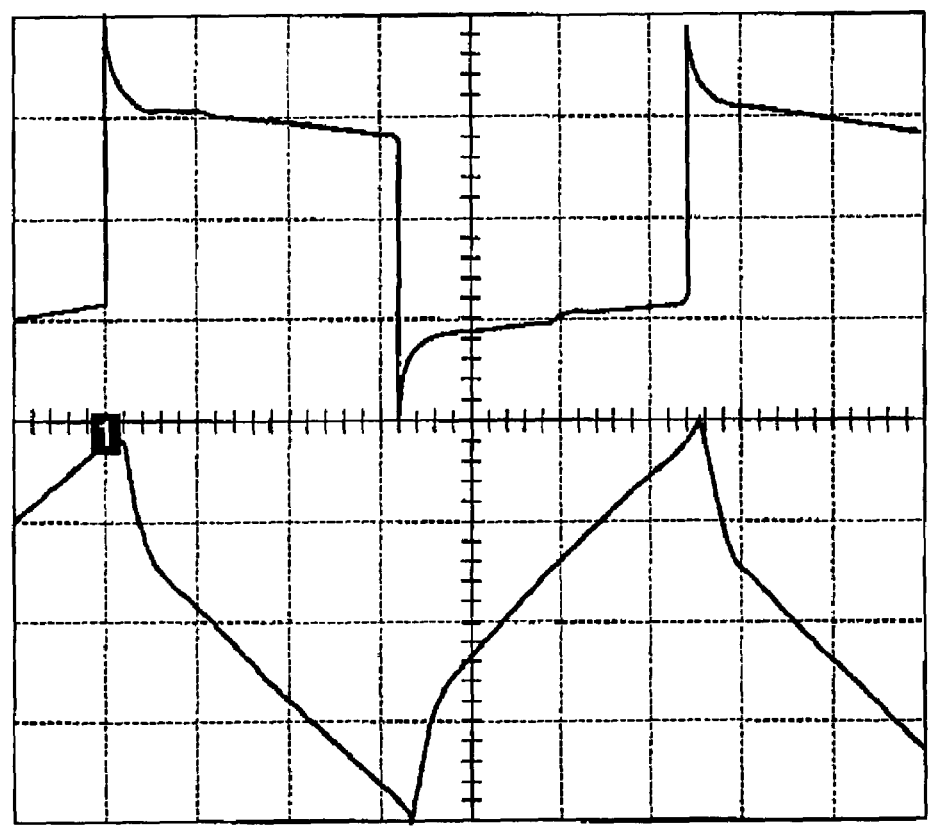
FIG. 7 shows the alternating influence of the interference signal and of the pumping current.

The probe model SM generates here a signal which comes as close as possible to the real interference signal as illustrated in FIG. 6. For this purpose, the signal source V12 firstly generates a square wave signal Phi1 with a frequency of 3 kHz and 0 V/5 V levels. This signal is then attenuated to, for example, 200 mV (ss) with 100 mV offset by means of a voltage divider R1/Ri. A further signal source Vs additionally generates an offset of, for example, 2.15 V. In this way, a square wave signal of 200 mV (ss) with an offset of 2.25 V, which corresponds to the conditions with a real lambda probe, is obtained at its output.

The square wave signal then passes to a filter network R14a, R14b, R14c, C14 and C15 which gives the square wave signal the desired curve form (square wave with time constant).

An amplifier AMP5b forms, together with resistors R14a, R14b and R304, an inverter so that the 3 kHz signal $\Delta Vs$ which is then filtered is produced with an amplitude of 200 mV (ss) at its output. Its noninverting input is at the center voltage Vm (2.25 V).

The compensation circuit KS itself is composed of two amplifiers AMP4a and AMP5a, four CMOS switches S3a, S3b, S3c, S3d, three resistors R22, R32, R302, and of two capacitors C50 and C51.

The inverting input of AMP4a, which acts as a buffer, is connected to its output so that it forms an amplifier with a gain factor of 1. (By inserting two resistors (not illustrated) between the inverting input and output or inverting input and Vm it is also possible to set the circuit to higher gain factors.

The noninverting input of AMP4a is connected via a resistor R302 to the output of AMP5b and via a resistor R22 to the output of the amplifier AMP5a. The noninverting input of AMP5a is at Vm. The inverting input is connected via a series circuit composed of C51 and R32 to the output of AMP4a as well as to the inputs of the switches S3b and S3d. The output of AMP5a is additionally connected to the inputs of the switches S3a and S3c.

The capacitor C50 is connected between the outputs of the switches S3a–S3b and the outputs of the switches S3c–S3d. The control inputs of S3a and S3d are connected to the signal source V12, and the control inputs of S3b and S3d are connected to Phi1 via one inverter (74HC04) each.

The controller R is connected downstream of this compensation circuit KS. The embodiment shown represents an integral controller which filters relatively high frequency components more strongly. It is composed of an amplifier AMP4b, resistors R41, R42 and a capacitor C12 . The noninverting input of AMP4b is connected to the center voltage Vm. The inverting input is connected via R41 to the output of AMP4a, and via a parallel circuit composed of R42 and C12 to the output of AMP4a. R42 is an equivalent resistor for the process of simulation, and it represents the finite amplification of AMP4b. It is not present in the real operation.

The core of the compensation circuit KS is the integrator which is composed of AMP5a, C50 and R32. The switches S3a, S3b, S3c, S3d form, together with the inverters 74HC04, an alternating switch. The latter periodically reverses the polarity of the capacitor C50 in synchronism with the oscillator signal Phi1 (3 kHz) between the inverting input of AMP5a and its output so that a voltage which is integrated at the capacitor C50 appears at the output of the integrator AMP5a as a square wave signal.

Switching over using the oscillator signal Phi1 also ensures that the integrator AMP5a integrates only signal components of $\Delta Vs$ which are phase-synchronous with respect to it. All other signal components are averaged out.

FIGS. 10 to 16 and the description are used to illustrate the mode of operation of the integrator Amp5a.

Figure 10:
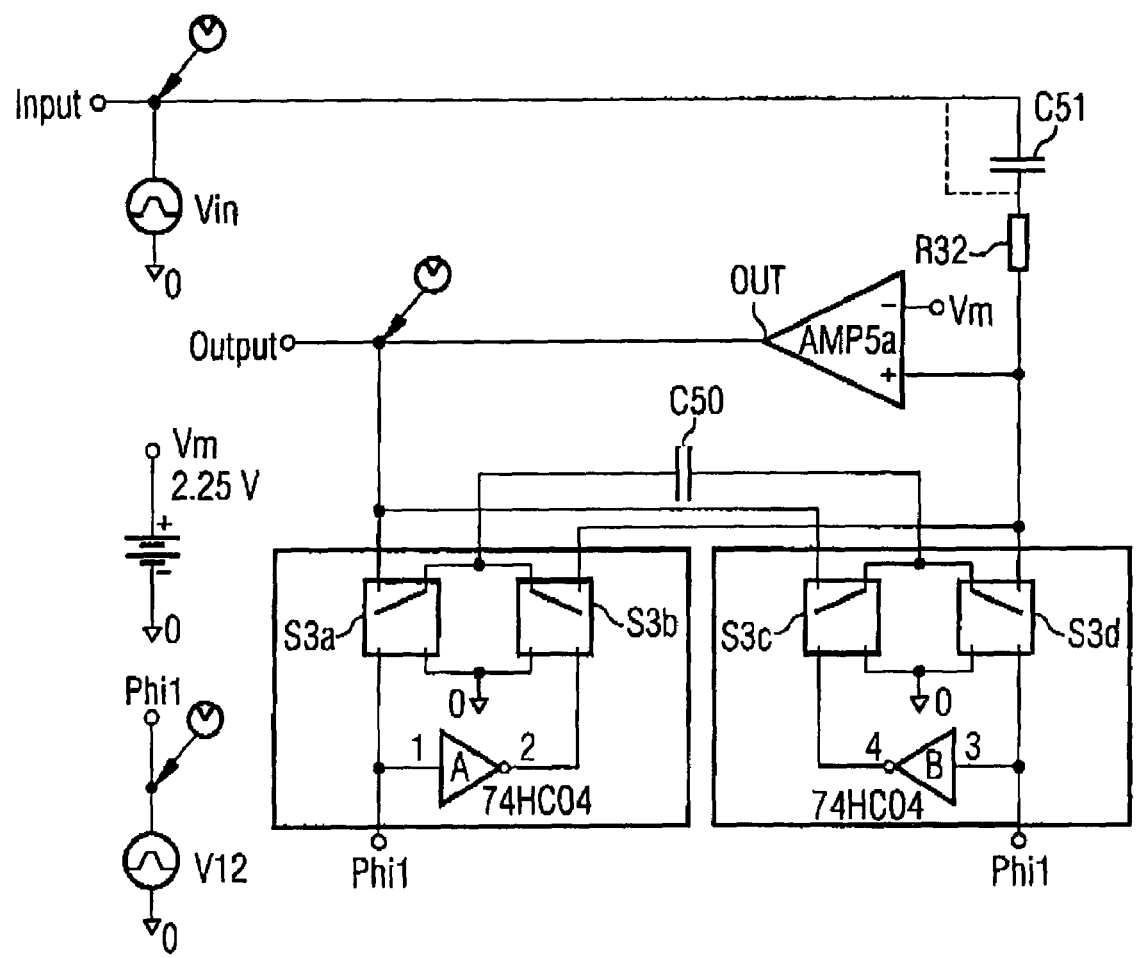
FIG. 10 shows the integrator from the compensation circuit according to FIG. 8.

The integrator illustrated once more in FIG. 10 is viewed without the signal feedback through the resistor R22. R302 and Amp4a are also omitted so that the actuation takes place directly at the capacitor C51, which is additionally bridged (dashed line) in order to be able to bring about the behavior in the case of DC voltage actuation which is shown in FIG. 11.

Figure 11:
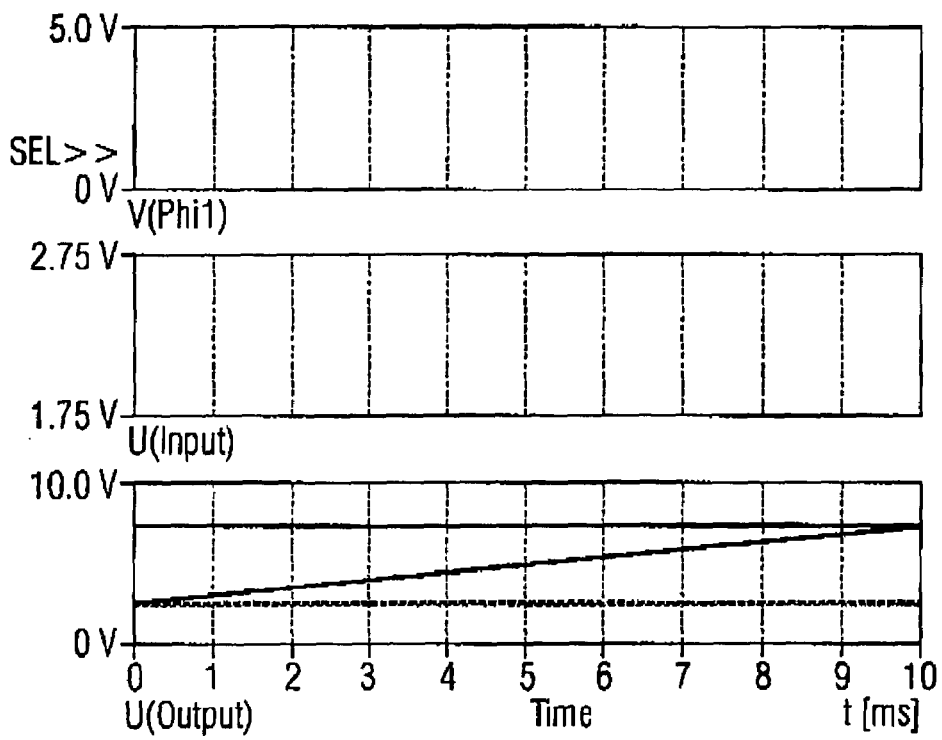
FIG. 11 shows the output signal of the integrator with the signal Phi1 switched off and the actuation signal constant at 1.75 V.

When the oscillator signal (Phi1—0V) is switched off, top of FIG. 11, the actuation signal Vin is a DC voltage with 1.75 V, in the center of FIG. 11. As the reference point of the integrator is at Vm=2.25 V (voltage at the noninverting input of Amp5a), the actuation voltage and its output voltage must also be referred to Vm.

The value of the actuation voltage referred to Vm is therefore $\Delta$Vin=1.75 V–Vref=–0.5 V. It is integrated with the time constant $\tau$=R32*C50. After the time T, the output voltage of the integrator reaches the value: $\Delta$Vout={–$\Delta$Vin*T/$\tau$}. Using the values selected in the example of $\Delta$Vin =–0.5 V, T=10 ms, R32=10 kOhm and C51=0.1 µF the following is obtained: $\Delta$Vout=5 V.

If the oscillator signal Phi1 is then connected into the circuit (top of FIG. 12), the integrating capacitor C50 is periodically switched over between the input and output of the integrator using the oscillator signal Phi1: each period of the signal $\Delta$Vs being integrated at the integrator Amp5a takes place in two phases.

Figure 12:
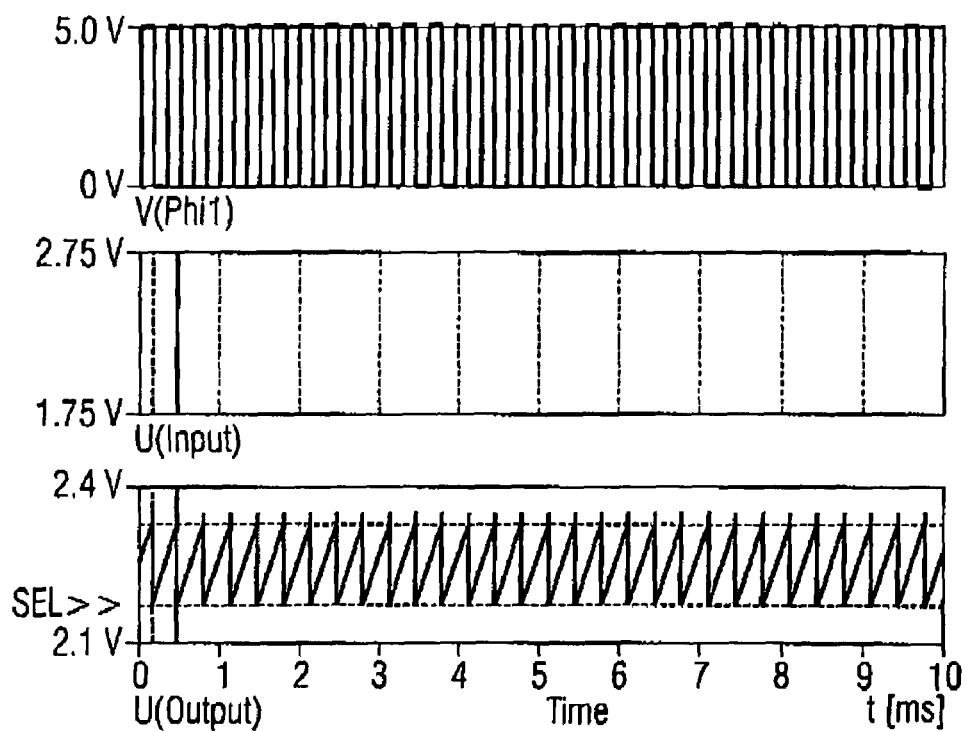
FIG. 12 shows the output signal of the integrator with the signal Phi1 switched on and the actuation signal constant at 1.75 V.
Figure 13:
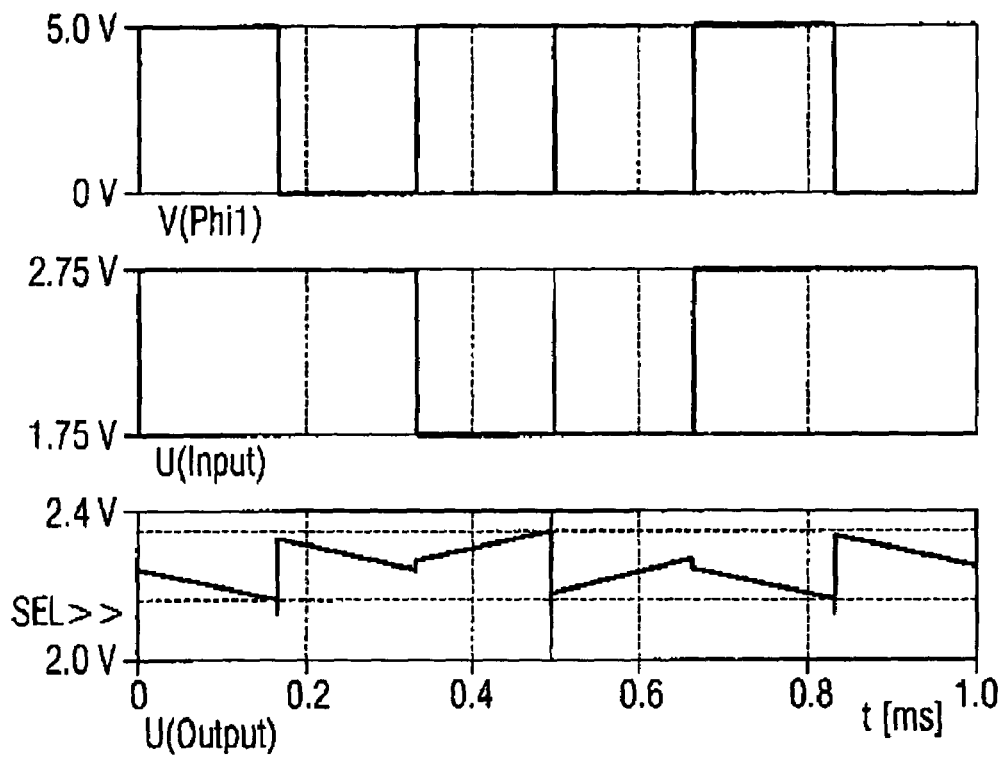
FIG. 13 shows the output signal of the integrator with the signal Phi1 switched on and the actuation signal 1.5 kHz.
Figure 14:
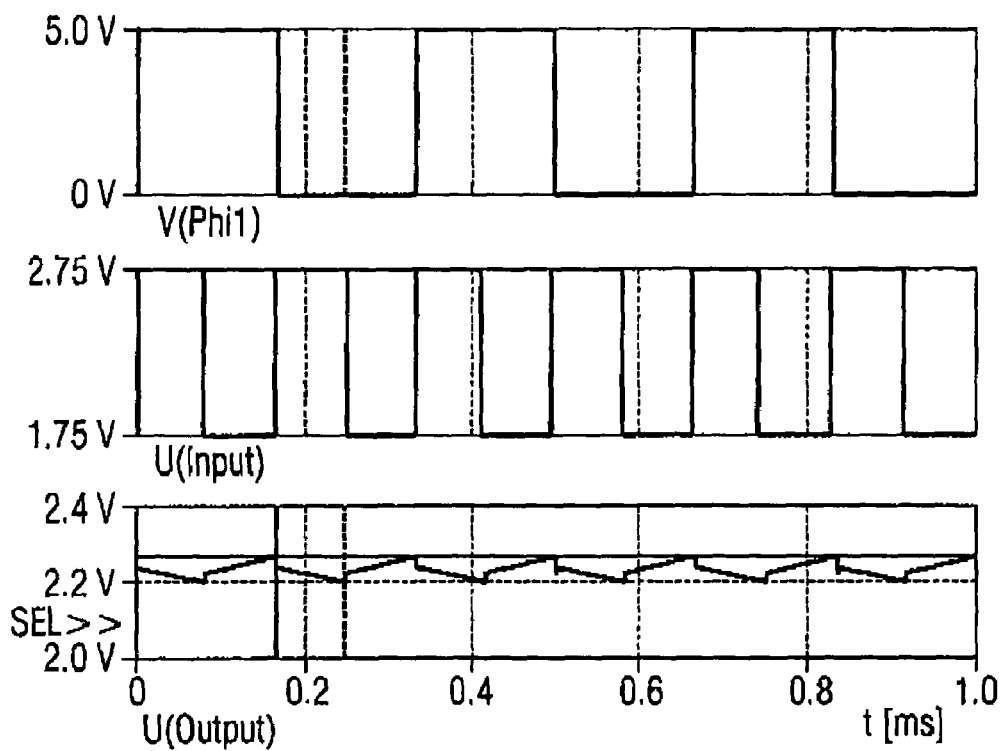
FIG. 14 shows the output signal of the integrator with the signal Phi1 switched on and the actuation signal 6 kHz.
Figure 15:
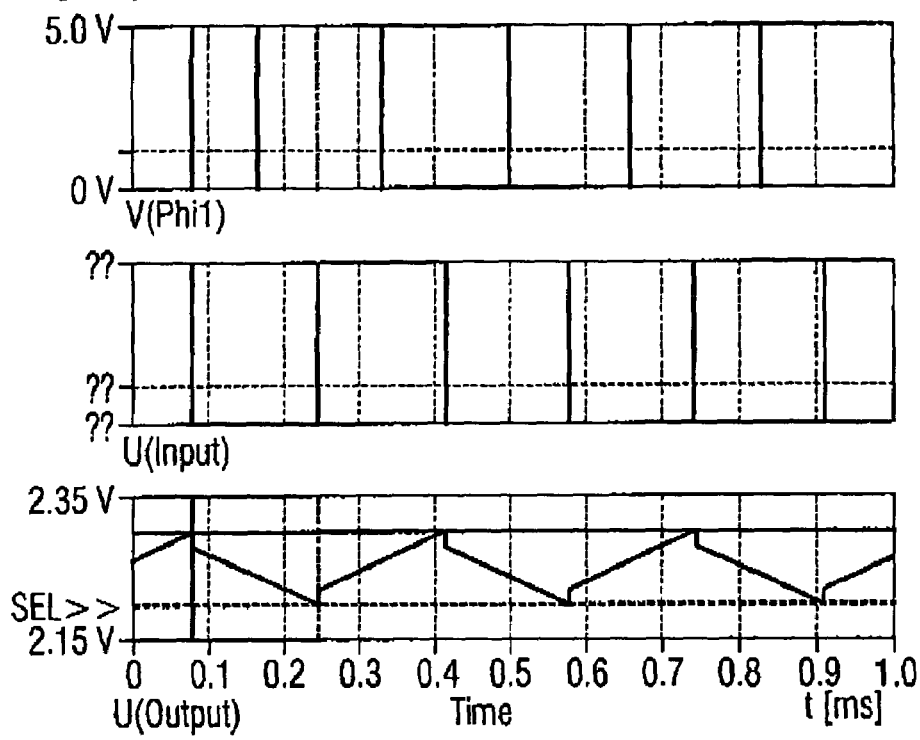
FIG. 15 shows the output signal of the integrator with the signal Phi1 switched on and the actuation signal 3 kHz-90° phase-shifted.

During the first phase (Phi1=0 V), $\Delta$Vin is integrated to approximately 2.34 V (Vm+0.09 V) at the output of Amp5a (bottom of FIG. 12).

At the start of the second phase (Phi1=5 V), the capacitor C50 is switched over and Vout jumps to approximately 2.17 V (Vm–0.08 V). Then (in the following signal period), integration is performed again in the following first phase up to 2.34 V etc.

On average, the output voltage therefore remains stable at 2.25 V despite the DC input voltage. $\Delta$Vout=(2.34 V–2.17 V)=0.17 V.

If the frequency of the actuation signal is changed, for example, to 1.5 kHz (center of FIG. 13) or 6 kHz (center of FIG. 14) in comparison with the oscillator signal Phi1 (top of FIG. 13, top of FIG. 14), only a relatively small, almost constant signal is also produced at the output of Amp5a. The cause of this is that the integrator averages over less (1.5 kHz) or more (6 kHz) than half a period of the actuation signal before it switches over. Correspondingly, the averaged residual amplitudes $\Delta$Vout (1.5 kHz) are at approximately 184 mV (bottom of FIG. 13) and $\Delta$Vout (6 kHz) at approximately 60 mV (bottom of FIG. 14). For AC voltage signals, the gain drops monotonously with 20 dB per decade of frequency increase.

If the phase angle between Phi1 (top of FIG. 15) and the actuation signal is changed via, for example, 90° (center of FIG. 15) while the frequency is the same, a residual amplitude $\Delta$Vout of 102 mV (bottom of FIG. 15) is obtained. The actuation signal is also averaged out here.

Figure 16:
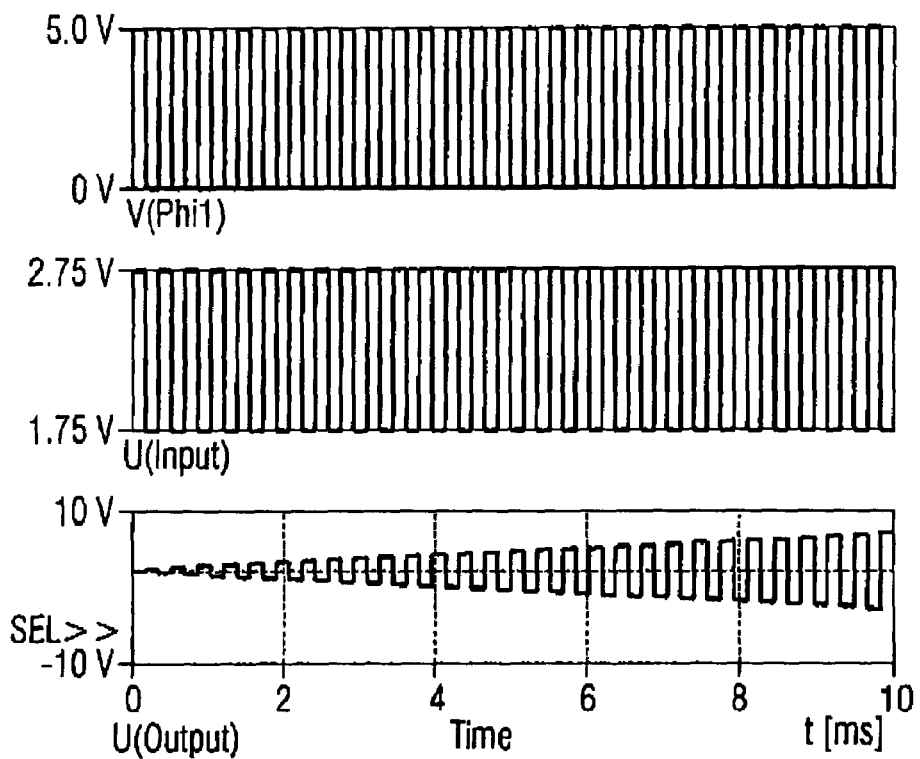
FIG. 16 shows the output signal of the integrator with the signal Phi1 switched on and the actuation signal 3 kHz without a phase shift.

Only if Phi1 and the actuation signal have the same frequency and phase angle, as illustrated at the top and in the center of FIG. 16, is a continuously increasing signal obtained at the integrator output (bottom of FIG. 16). The integration phase and signal phase have identical profiles so that averaging is not carried out but instead integration, which is analogous to actuating with DC voltage.

Since the actuation signal Vin and the integrator have the same reference potential (2.25 V), the connection can be made by means of the capacitor C51. In this way, the influence of any control error of the pumping current control ($\Delta$Vs) is reduced without disadvantages.

The function of the integrator in the real compensation circuit (FIGS. 5 and 8) is explained from the behavior of the integrator as described in FIGS. 10 to 16.

As long as the actuation signal Vin does not have any signal components which are frequency-synchronous and phase-synchronous with the oscillator signal Phi1, the output of the integrator Amp5a will only have a DC voltage (with Vm=2.25 V). The output impedance of Amp5a is small here. The signal $\Delta$Vs passes via the resistor R302 (FIG. 8) to the noninverting input of Amp4a, and it is attenuated by the voltage dividers R302, R22. If the resistors R302 and R22 have the same value, the attenuation is 50%.

From the output of the amplifier Amp4a, said signal passes onto the input of the controller R. Overall, the compensation signal for $\Delta$Vs therefore only has the effect of a voltage divider. However, this is without significance as the amplitude loss can be compensated by a suitable configuration of the controller R.

However, if the actuation signal Vin has signal components which are frequency-synchronous and phase-synchronous with the oscillator signal Phi1, for example, the 3 kHz signal, acting as interference signal, of the Ris measurement (FIG. 6), this component is integrated at the integrator Amp5a. A 3 kHz square wave signal with rising amplitude and phase-shifted with respect to the interference signal contained in the differential signal $\Delta$Vs by 180° appears at the output of Amp5a.

As a consequence of this output signal, the 3 kHz amplitude at the noninverting input of Amp4a is reduced. Correspondingly, the 3 kHz amplitude at the output of Amp4a also drops so that the actuation signal of the integrator Amp5a is also reduced.

Ultimately, a state of equilibrium is established, the interference signal component in $\Delta$Vs and the compensation signal (3 kHz output signal of the integrator Amp5a) being largely cancelled out so that only a residual signal remains at the integrator input and thus at the output of the compensation circuit. On the other hand, all the other frequency components of $\Delta$Vs are only attenuated by the 50% described above.

The control loop which is produced in this way compensates the interference signal completely if the curve shape is a rectangle. However, as this is not the case in practice, the compensation can be improved by approximating it incrementally to the real curve profile.

Figure 17:
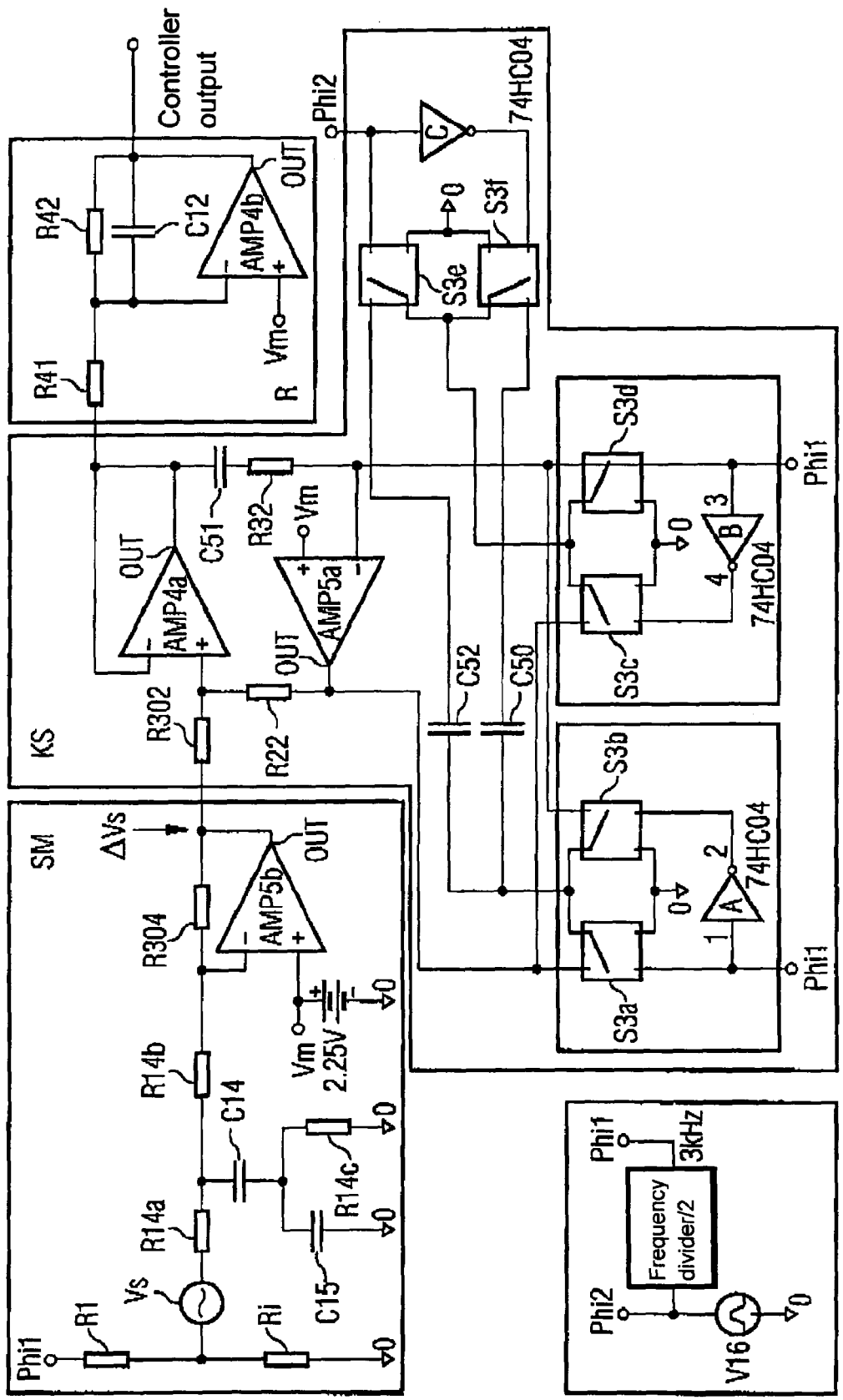
FIG. 17 shows a two-stage compensation circuit.

An expansion to multi-step characteristics (a plurality of integration phase sections per signal period) is carried out by adding at least one further capacitor and further changeover switches to the integrator and incrementally carrying out the integration of the 3 kHz signal using these capacitors. A corresponding circuit is illustrated in FIG. 17.

A further capacitor C52 is inserted, one terminal of which capacitor C52 is connected to the outputs of the switches S3a, S3b, in parallel with the capacitor C50. The other terminal of C50 is then no longer connected to the outputs of the switches S3c, S3d, but rather to the input of a switch S3f. The other terminal of C52 is likewise connected to the input of a switch S3e. The outputs of S33 and S3f are connected to the outputs of S3c, S3d. The control input of S3e is connected to a further signal source V15 which generates an oscillator signal Phi2 with a frequency of 6 kHz. The control input of S3f is also connected to the signal source V15 via a further inverter (74HC04). The oscillator signal (Phi1=3 kHz) can be generated, for example, by halving the 6 kHz oscillator signal (Phi2) by means of a frequency divider (FIG. 17).

By means of this expansion, the integration of each period of the signal $\Delta$Vs at the integrator Amp5a is then decomposed into 4 phase sections:

In the phase section 1 (0%–25% of the period length of the oscillator Phi1) it will be assumed that capacitor C50 is connected to the other circuit via switch S3f. Said capacitor C50 is therefore active as an integrating capacitor. Due to the control effect of the compensation circuit KS, a phase-synchronous amplitude value which corresponds to the value (low at this time owing to the time constant) of the interference signal is produced at the output of AMP5a.

In phase section 2 (25%–50%), switch S3f is opened and switch S3e is closed as a result of the level change of the signal source V15. Now, capacitor C52 is active as the integrating capacitor. It then integrates the (risen) value of the interference signal. Correspondingly, the output voltage of the integrator is somewhat higher in this phase.

Phase section 3 (50%–75%) corresponds to phase section 1, but now, due to the position of the alternating switches, the capacitor C52 is active as an integrating capacitor and the amplitude of the integrator output jumps from positive to negative.

Phase section 4 (75%–100%) corresponds in turn to phase section 2 (C52 active), the amplitude being also negative here.

The switch positions in the individual phases can be found in the following table.

|  | S3a | S3b | S3c | S3d | S3e | S3f |
|---|---|---|---|---|---|---|
| Phase section 1 | On | Off | Off | On | Off | On |
| Phase section 2 | On | Off | Off | On | On | Off |
| Phase section 3 | Off | On | On | Off | Off | On |
| Phase section 4 | Off | On | On | Off | On | Off |

Figure 18:
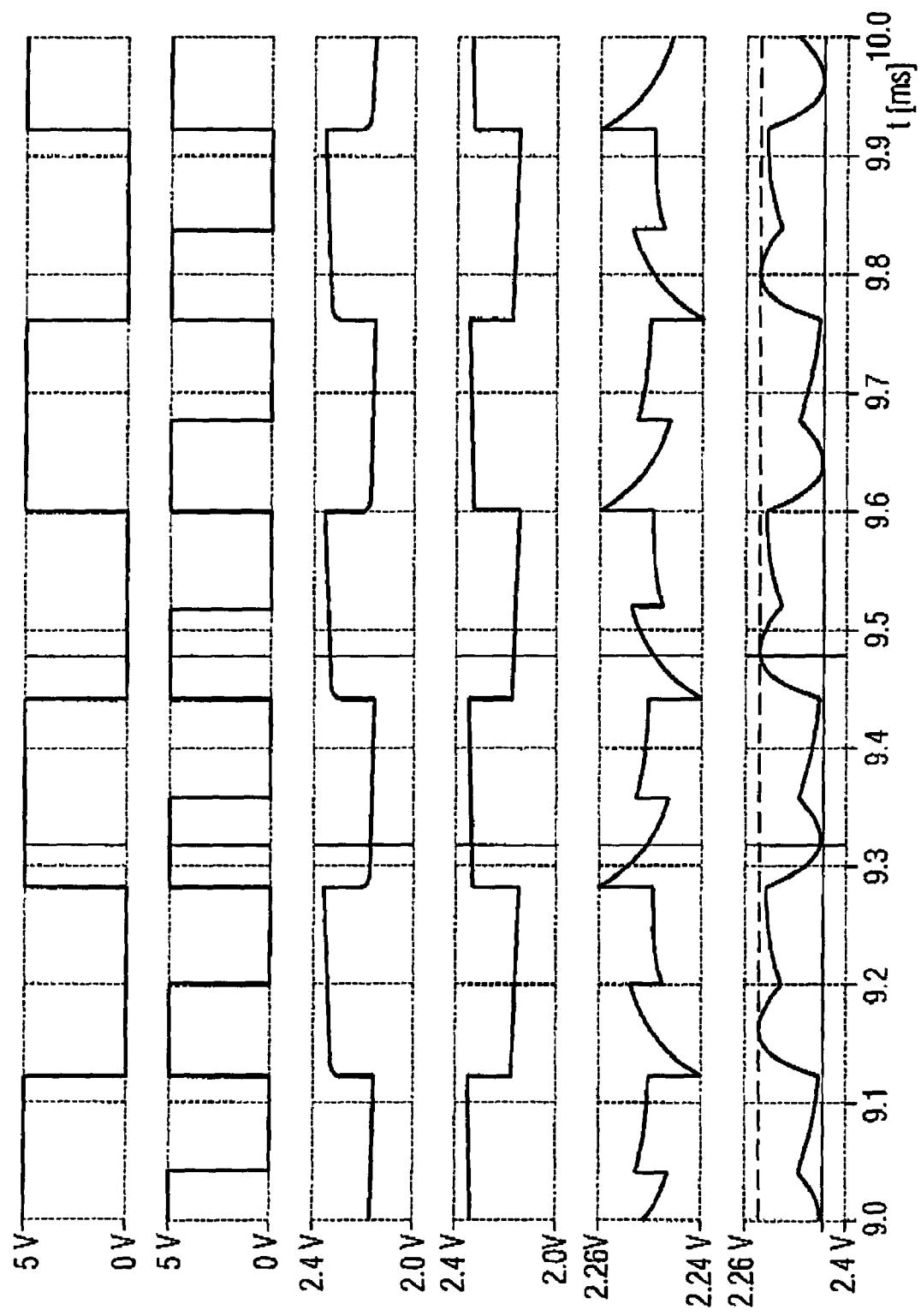
FIG. 18 shows the signal profiles for the two-stage compensation.

Thus, the curve profile of the compensation signal illustrated in FIG. 18, track 4 is obtained. As a result of this, the (filtered) residual signal is reduced from approximately 30 mV (ss) for single-switch compensation to approximately 13 mV (ss) for dual-switch compensation, that is to say via further 7 dB. Overall, the interference signal is then attenuated by 16dB+7dB=23 dB.

FIG. 18 shows the following signals:

| | |
|---|---|
| Track 1: | oscillator signal Phi1 = 3 kHz, |
| Track 2: | oscillator signal Phi2 = 6 kHz, |
| Track 3: | interference signal contained in the differential signal $\Delta$Vs, |
| Track 4: | compensation signal of two-stage composition (at the output of the integrator Amp5a), |
| Track 5: | residual signal at the output of the compensation circuit, and |
| Track 6: | residual signal at the output of the controller after further filtering. |

A further subdivision of the integration intervals leads to an increase in the improvement in this attenuation, but also to greater expenditure on hardware and software.

In addition to the implementational example presented, alternative embodiments of the invention are also conceivable.

Figure 19:
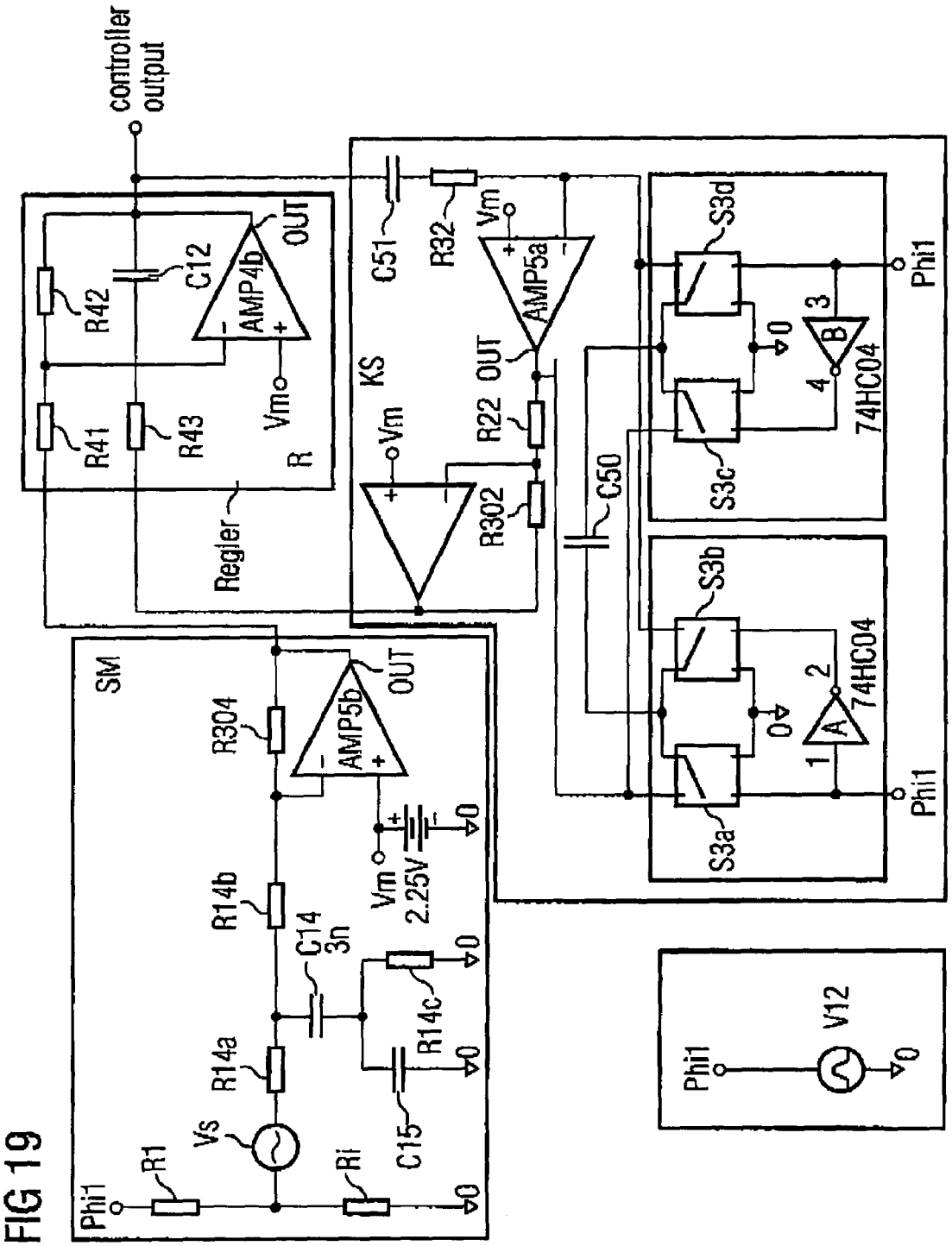
FIG. 19 shows a compensation circuit which is integrated into the controller.

For example, the compensation circuit can be combined with the controller R. In FIG. 19, the integration of the compensation circuit according to FIG. 8 is combined with the controller R, as a result of which the amplitude loss, due to the voltage dividers R302, R22 from FIG. 8, is avoided.

In contrast with the circuit illustrated in FIGS. 8 and 17, the amplifier Amp4a is not operated here as a buffer but rather as an inverter by means of the resistors R22 and R302. Its noninverting input is at the center voltage Vm (2.25 V). The output of the inverter Amp4a constitutes the output of the compensation circuit and is connected via a resistor R43 to the inverting input of the controller Amp4b, in the same way as R41 has already been connected. As a result, the controller is expanded to form a summing element. The output of the controller is connected to the capacitor C51, the input of the compensation circuit. The compensation effect then takes place as a result of the summing property of the controller R.

The invention as described can be used not only in a circuit arrangement for compensating interference signals in the control loop of a linear lambda probe but also quite generally in control circuits for compensating interference variables.

The invention claimed is:

1. A circuit arrangement for compensating interference signals in the control loop of a linear lambda probe comprising:
   an evaluation circuit with a differential amplifier which forms the difference between a Nernst voltage which is subjected to an interference signal and a reference voltage,
   a controller generating a controlling voltage from the difference wherein the controlling voltage is converted into a pumping current by a subsequent pumping current source said pumping current being fed back to said linear lambda probe,
   a compensation circuit, coupled between the output of the differential amplifier and the input of the controller, for generating a compensation signal which is approximated in its curve profile to the interference signal and has an amplitude and frequency which are identical to the interference signal but phase-shifted through 180°, and for subtracting the compensation signal from the differential signal, wherein the compensation circuit comprises an amplifier which is connected as a buffer and an integrator, the differential signal and the output signal of the integrator are fed to the input of the buffer amplifier, and wherein the output signal of the buffer amplifier is fed to the inverting input of the integrator and to the input of the controller.

2. The circuit arrangement as claimed in claim 1, wherein the integrator contains an integration capacitor and switching means to reverse the polarity ot the integration capacitor in synchronism with an oscillator frequency of an oscillator signal, wherein the circuit arrangement is operable to connect, in a one—positive—phase, the one terminal of the integration capacitor to the output of the integrator and the other terminal to the inverting input of the integrator, and in a other—negative—phase, to connect the one terminal to the inverting input and the other terminal to the output of the integrator.

3. The circuit arrangement as claimed in claim 2, wherein the interference signal and the oscillator signal are generated by means of a single signal source.

4. The circuit arrangement as claimed in claim 1, wherein the integrator comprises at least two integration capacitors and switching means for reversing a polarity of each of the at least two integration capacitors in synchronism with an oscillator frequency, the circuit arrangement being operable to connect, in identical numbers of phase sections, corresponding to the number of integration capacitors, during a one—positive—phase, the first terminals of the integration capacitors to the output of the integrator and successively the other terminals to the inverting input of the integrator, during a other—negative—phase, to connect the first terminals to the inverting input and successively the other terminals to the output of the integrator.

5. The circuit arrangement as claimed in claim 4, wherein the interference signal and the oscillator signal are generated by means of a single signal source.

6. A method for compensating interference signals in the control loop of a linear lambda probe comprising the steps of:
   forming the difference between a Nernst voltage which is subjected to an interference signal and a reference voltage,
   generating a controlling voltage from the difference,
   converting the controlling voltage into a pumping current,
   generating a compensation signal which is approximated in its curve profile to the interference signal and has an amplitude and frequency which are identical to the interference signal but phase-shifted through 180°, wherein the compensation signal is subtracted from the differential signal and as a result largely cancels out the interference signal, wherein the compensation signal is formed by the steps of:
   feeding the difference to a buffer amplifier generating a buffered signal,
   integrating the buffered signal and feeding the integrated signal back to said buffer amplifier,
   feeding the buffered signal to an input of a controller.

7. A method according to claim 6, wherein the step of integrating is performed by switching the polarity of a capacitor in the feedback loop of an operational amplifier from a first polarity during a—positive—phase to a second polarity during another—negative—phase.

8. A method according to claim 6, wherein the step of integrating is performed by reversing a polarity of each of at least two capacitors in the feedback loop of an operational amplifier in synchronism with an oscillator frequency whose phase is divided in identical numbers of positive and negative phase sections corresponding to the number of integration capacitors, wherein the capacitors are sequentially coupled in the feedback loop with a first polarity during sections of a positive phase and are sequentially coupled in the feedback loop with a second polarity during sections of a negative phase.

9. A circuit arrangement for compensating interference signals in the control loop of a linear lambda probe comprising:
   an evaluation circuit with a differential amplifier which forms the difference between a Nernst voltage which is subjected to an interference signal and a reference voltage,
   a controller generating a controlling voltage from the difference wherein the controlling voltage is converted into a pumping current by a subsequent pumping current source said pumping current being fed back to said linear lambda probe,
   a compensation circuit, coupled between the output of the differential amplifier and the input of the controller, for generating a compensation signal which is approximated in its curve profile to the interference signal and has an amplitude and frequency which are identical to the interference signal but phase-shifted through 180°, and for subtracting the compensation signal from the differential signal, wherein the controller is combined with the compensation circuit which contains an amplifier which is connected as an inverter and an integrator, the controller is connected as a summing amplifier to two inputs, the differential signal is fed to the one input of the controller, and wherein the output signal of the controller is fed to the input of the integrator whose output signal is fed to the second input of the controller via the inverter.

10. The circuit arrangement as claimed in claim 9, wherein the integrator contains an integration capacitor and switching means to reverse the polarity of the integration capacitor in synchronism with an oscillator frequency of an oscillator signal, wherein the circuit arrangement is operable to connect, in a one—positive—phase, the one terminal of the integration capacitor to the output of the integrator and the other terminal to the inverting input of the integrator, and in a other—negative—phase, to connect the one terminal to the inverting input and the other terminal to the output of the integrator.

11. The circuit arrangement as claimed in claim 10, wherein the interference signal and the oscillator signal are generated by means of a single signal source.

12. The circuit arrangement as claimed in claim 9, wherein the integrator comprises at least two integration capacitors and switching means for reversing a polarity of each of the at least two integration capacitors in synchronism with an oscillator frequency, the circuit arrangement being operable to connect, in identical numbers of phase sections, corresponding to the number of integration capacitors, during a one—positive—phase, the first terminals of the integration capacitors to the output of the integrator and successively the other terminals to the inverting input of the integrator, during a other—negative—phase, to connect the first terminals to the inverting input and successively the other terminals to the output of the integrator.

13. The circuit arrangement as claimed in claim 12, wherein the interference signal and the oscillator signal are generated by means of a single signal source.

14. A method for compensating interference signals in the control loop of a linear lambda probe comprising the steps of:
forming the difference between a Nernst voltage which is subjected to an interference signal and a reference voltage,
generating a controlling voltage from the difference,
converting the controlling voltage into a pumping current,
generating a compensation signal which is approximated in its curve profile to the interference signal and has an amplitude and frequency which are identical to the interference signal but phase-shifted through 180°, wherein the compensation signal is subtracted from the differential signal and as a result largely cancels out the interference signal, wherein the controlling voltage is formed by a forming a further difference between said difference and the compensation signal;
and the compensation signal is formed by
integrating the controlling voltage and amplifying the integrated voltage.

15. A method according to claim 14, wherein the step of integrating is performed by switching the polarity of a capacitor in the feedback loop of an operational amplifier from a first polarity during a—positive—phase to a second polarity during another—negative—phase.

16. A method according to claim 14, wherein the step of integrating is performed by reversing a polarity of each of at least two capacitors in the feedback loop of an operational amplifier in synchronism with an oscillator frequency whose phase is divided in identical numbers of positive and negative phase sections corresponding to the number of integration capacitors, wherein the capacitors are sequentially coupled in the feedback loop with a first polarity during sections of a positive phase and are sequentially coupled in the feedback loop with a second polarity during sections of a negative phase.

* * * * *